US00PP10429P

United States Patent [19]

Kientzler

[11] Patent Number: Plant 10,429

[45] Date of Patent: Jun. 2, 1998

[54] NEW GUINEA IMPATIENS PLANT 'KIMPGUA'

[75] Inventor: Ludwig Kientzler, Gensingen, Germany

[73] Assignee: Paul Ecke Ranch, Inc., Encinitas, Calif.

[21] Appl. No.: 796,075

[22] Filed: Feb. 5, 1997

[51] Int. Cl.[6] ..... A01H 5/00

[52] U.S. Cl. ..... Plt./87.6

[58] Field of Search ..... Plt./87.6

*Primary Examiner*—James R. Feyrer
*Attorney, Agent, or Firm*—C. A. Whealy

[57] ABSTRACT

A new and distinct cultivar of New Guinea impatiens plant named 'Kimpgua', a.k.a 'Improved Guadeloupe' characterized by its flat and rounded purple and pink bi-colored flowers; upright and outwardly spreading growth habit; freely branching plant habit; and dark green, slightly glossy, non-variegated foliage.

2 Drawing Sheets

The present invention relates to a new and distinct cultivar of New Guinea Impatiens plant, botanically known as *Impatiens hawkeri*, which is to be internationally registered as 'Kimpgua'. It is anticipated that the plant will be marketed under the synonym 'Improved Guadeloupe'. Hereinafter the disclosed plant will be referred to as 'Improved Guadeloupe'.

The new cultivar is a product of a planned breeding program conducted by the inventor in Gensingen, Germany. The objective of the breeding program was to develop new varieties that have a uniform plant habit, attractive flower colors, good flower form and numerous flowers per plant.

The new cultivar originated from a cross made by the inventor of the commercial cultivar Guadeloupe (U.S. Plant patent applied for) as the male, or pollen parent, with the proprietary seedling selection identified as N213 as the female, or seed patent. The cltivar Improved Guadeloupe was discovered and selected by the inventor as a flowering plant within the progeny of the stated cross in a controlled environment in Gensingen, Germany. Asexual reproduction of the new cultivar by terminal cuttings taken at Gensingen, Germany, has shown that the unique features of this new Impatiens are stable and reproduced true to type in successive generations of asexual reproduction.

The following traits have been repeatedly observed and are determined to be the unique characteristics of 'Improved Guadeloupe'. These characteristics in combination distinguish 'Improved Guadeloupe' as a new and distinct cultivar:

1. Flat and rounded purple and pink bi-colored flowers.
2. Upright and outwardly spreading growth habit.
3. Freely branching plant habit.
4. Dark green, slightly glossy, non-variegated foliage.

The new New Guinea Impatiens is similar in flower color to the male parent, the New Guinea Impatiens cultivar 'Guadeloupe'. However in side-by-side comparisions in Encinitas, Calif., under commercial practice, plants of the new New Guinea Impatiens differed from plants of the cultivar 'Guadeloupe' in the following characteristics:

1. Plants of the new New Guinea Impatiens more outwardly spreading than plants of the cultivar 'Guadeloupe'.
2. Plants of the new New Guinea Impatiens are more freely branching than plants of the cultivar 'Guadeloupe'.
3. Stems of plants of the new New Guinea Impatiens are green whereas stems of plants of the cultivar 'Guadeloupe' are dark purple.
4. Leaves of plants of the new New Guinea Impatiens are larger than leaves of plants of the cultivar 'Guadeloupe'.
5. Abaxial surface of leaves of plants of the new New Guinea Impatiens are dark green whereas upper surfaces of leaves of plants of the cultivar 'Guadeloupe' are dark reddish green.

6. Plants of the new New Guinea Impatiens are more freely flowering than plants of the cultivar 'Guadeloupe'.
7. Flowers of plants of the new New Guinea Impatiens are rounded and flat whereas flowers of plants of the cultivar 'Guadeloupe' are star-shaped and slightly cupped.
8. Although both bi-colored cultivars, actual flower colors and patterns are different for each variety.
9. Peduncles of plants of the new New Guinea Impatiens are longer than peduncles of plants of the cultivar 'Guadeloupe'.

The new New Guinea Impatiens is also similar in flower color to the New Guinea Impatiens cultivar 'Octavia' (disclosed in U.S. Plant Pat. No. 8,430). However in side-by-side comparisons in Encinitas, Calif., under commercial practice, plants of the new New Guinea Impatiens differed from plants of the cultivar 'Moorea' in the following characteristics:

1. Plants of the new New Guinea Impatiens are more freely branching than plants of the cultivar 'Octavia'.
2. Stems of plants of the new New guinea Impatiens are green whereas stems of plants of the cultivar 'Octavia' are dark purple.
3. Plants of the new New Guinea Impatiens are more freely flowering than plants of the cultivar 'Octavia'.
4. Flowers of plants of the new New Guinea Impatiens are rounded and flat whereas flowers of plants of the cultivar 'Octavia' are star-shaped and slightly cupped.
5. Although both bi-colored cultivars, actual flower colors and patterns are different for each variety.
6. Peduncles of plants of the new New Guinea Impatiens are longer than peduncles of plants of the cultivar 'Octavia'.

A detailed comparision of plants of the new New Guinea Impatiens and the cultivars Guadeloupe and Octavia appears in Chart A at the end of the specification.

The accompanying colored photographs illustrate the overall appearance of the new cultivar, showing the colors as true as it is reasonably possible to obtain in colored reproductions of this type.

The first photograph comprises a top perspecive view of a typical plant of 'Improved Guadeloupe'.

The second photograph comprises a close-up view of typical flowers and leaves of the varieties Guadeloupe (top of photo) and 'Improved Guadeloupe' (bottom of photo).

The flower and foliage colors in the photographs may differ from the actual colors due to light reflectance.

The cultivar 'Improved Guadeloupe' has not been observed under all possible environmental conditions. The phenotype may vary somewhat with variations in environment such as temperature and light intensity, without, however, any variance in genotype. The following observations, measurements and comparisons describe plants grown 10-cm pots in Encinitas, Calif., under commercial practice in a fiberglass-covered greenhouse with day temperatures ranging from 23 to 29C and night temperatures ranging from 16 to 18C and light levels averaging 3,000 footcandles.

In the following description, color references are made to The Royal Horticultural Society Colour Chart except where general terms of ordinary dictionary significance are used.

Classification:

*Botanical.*—*Impatiens hawkeri.*

*Commercial.*—New Guinea Impatiens 'Kimpgua', marketed under 'Improved Guadeloupe'.

Parentage:

*Male parent.*—*Impatiens hawkeri* 'Guadeloupe' (U.S. Plant patent applied for).

*Female parent.*—Proprietary seedling selection N213.

Propagation:

*Type cutting.*—Terminal cuttings.

*Time to initiate roots.*—About 15 days with 21C soil temperature.

Plant description:

*Plant form.*—Upright and outwardly spreading, rounded and mounding.

*Growth habit.*—Moderately vigorous. Moderate to freely branching, dense and bushy growth. Suitable for 10 to 25-cm containers.

*Plant size.*—Height: About 21 cm. Width or spread: About 29 cm.

*Lateral branches.*—Quantity: About seven. Size: Length: About 13 cm. Diameter: About 1.1 cm. Internode length: About 5 cm. Color: 146B with flight red, 59A, stripes.

*Foliage description.*—Leaves simple, generally symmetrical, abundant, opposite or in whorls of three, horizontal to plant and flat in aspect. Size, largest leaves: Length: 11.5 to 12.5 cm. Width: About 5 cm. Shape: Ovate with acuminate apex, attenuate base and ciliate margin. Texture: Smooth, slightly glossy. Color: Young foliage, upper surface: 146A. Young foliage, lower surface: 185A. Fully expanded foliage, upper surface: 147A. Fully expanded foliage, lower surface: 184B. Venation, upper surface: 53B. Venation, lower surface: 53A. Petiole: Size: Length: 3 to 3.5 cm. Diameter: About 3.5 mm. Color: 53C/53D.

Flower description:

*Flower type and habit.*—Large purple and pink bi-colored flowers. Freely and continuously flowering. Flowers arise from leaf axils. Usually ten flowers per lateral branch. Flowers positioned at or above the foliage and face upward or outward. Flowers flat and rounded. Flowers persistent.

*Flowering season.*—Year-round under greenhouse conditions. In the garden, flowering is continuous from spring until fall.

*Flower size.*—Length: About 6 cm. Width: About 6 cm. Depth: About 5 mm.

*Flower buds.*—Size: Length: About 2.4 cm. Diameter: About 1.2 cm. Shape: Ovoid. Color: 67A.

*Petals.*—Quantity: Five. Size (largest petals): Length: Top petal: About 2.8 cm. Middle petals: About 3 cm. Bottom petals: About 3.2 cm. Width: Top petal: About 5 cm. Middle petals: About 3.5 cm. Bottom petals: About 4 cm. Shape: Cordate with emarginate apex, cuneate or obtuse base and entire margin. Texture: Satiny, smooth. Color: When opening, upper surface: Iridescent, 80B with 66A centers and stripe. When opening, lower surface: Iridescent, 80D with 52A at center. Fully opened, upper surface: Iridescent, 80C with 66A centers and stripe. Fully opened, lower surface: Iridescent, 68A with 52A at center. Fading to: Iridescent, 81D.

*Spur.*—Length: About 5 cm. Shape: Narrow and curved. Color: Proximal: 52B. Center: 144C. Distal: 144A.

*Peduncles.*—Length: About 5.7 cm. Angle: Erect and outward. Strength: Strong. Color: 144B with some red, 53B, stripes.

*Reproductive organs.*—Androecium: Stamen number: Five, anthers fused, filaments free. Anther shape: Obovate. Anther size: 6 by 3 mm. Anther color: Cream. Amount of pollen: Moderate. Pollen color: Creamy white. Gynoecium: Five-loculate fused. Stigma color: White. Gynoecium length: About 5 mm. Gynoecium color: 187A.

Disease resistance: Under commercial conditions, resistance nor susceptibility to pathogens has not been observed.

Seed development: Seed production is not usually observed.

CHART A

| CHARACTERISTIC | 'IMPROVED GUADELOUPE' | 'GUADELOUPE' | 'OCTAVIA' |
|---|---|---|---|
| GROWTH HABIT | Upright and outwardly spreading | Upright | Upright and outwardly spreading |
| BRANCHING HABIT | Moderate, 7 lateral branches per plant | Low, 4 to 5 lateral branches per plant | Low, 4 to 5 lateral branches per plant |
| STEM COLOR | 146B with slight stripes, 59A | 187A | 187B |
| LEAF LENGTH | 11.5 to 12.5 cm | 9.5 to 10 cm | 10 to 11 cm |
| LEAF WIDTH | About 5 cm | About 4.3 cm | 4.5 to 5 cm |
| LEAF COLOR, YOUNG, UPPER SURFACE | 146A | 147A | 147A |
| LEAF COLOR, YOUNG, LOWER SURFACE | 185A | 184A with green | 187A |
| LEAF COLOR, FULLY EXPANDED, UPPER SURFACE | 147A | 187A with green | 147A |
| LEAF COLOR, FULLY EXPANDED, LOWER SURFACE | 184B | 183B | 183A |
| VENATION COLOR, UPPER SURFACE | 53B | 60B | 187C |
| VENATION COLOR, LOWER SURFACE | 53A | 60B | 187B |
| PETIOLE LENGTH | 3 to 3.5 cm | About 2.8 cm | 3 to 4 cm |
| PETIOLE DIAMETER | About 3.5 mm | About 3 mm | About 3 cm |
| PETIOLE COLOR | 53C/53D | 60B | 187D |
| QUANTITY OF FLOWERS PER LATERAL STEM | About 10 | About 8 | About 8 |
| FLOWER SHAPE | Rounded | Star-shaped | Star-shaped |
| FLOWER ASPECT | Flat | Slightly cupped | Slightly cupped |
| PETAL COLOR, WHEN OPENING, UPPER SURFACE | 80B with 66A centers | 84B with 67A centers | 81C with 57A centers |
| PETAL COLOR, | 80D with 52A | 80C with 47A | 57A centers, |

CHART A-continued

| CHAR-ACTERISTIC | 'IMPROVED GUADELOUPE' | 'GUADELOUPE' | 'OCTAVIA' |
|---|---|---|---|
| WHEN OPENING, LOWER SURFACE | centers | centers | 77C at edges |
| PETAL COLOR, OPENED, UPPER SURFACE | 80C with 66A centers | 84B with darker than 66A centers | 75A with 57A centers |
| PETAL COLOR, OPENED, LOWER SURFACE | 68A with 52A centers | 67C with 50A centers | 52A centers, 67B at edges |
| PETAL COLOR, FADING TO | 81D | 82C | 82C |

CHART A-continued

| CHAR-ACTERISTIC | 'IMPROVED GUADELOUPE' | 'GUADELOUPE' | 'OCTAVIA' |
|---|---|---|---|
| PEDUNCLE LENGTH | About 5.7 cm | About 4 cm | About 5 cm |
| FLOWER BUD COLOR | 67A | 46B | 57A |

It is claimed:

1. A new and distinct cultivar of New Guinea Impatiens plant, as illustrated and described.

* * * * *

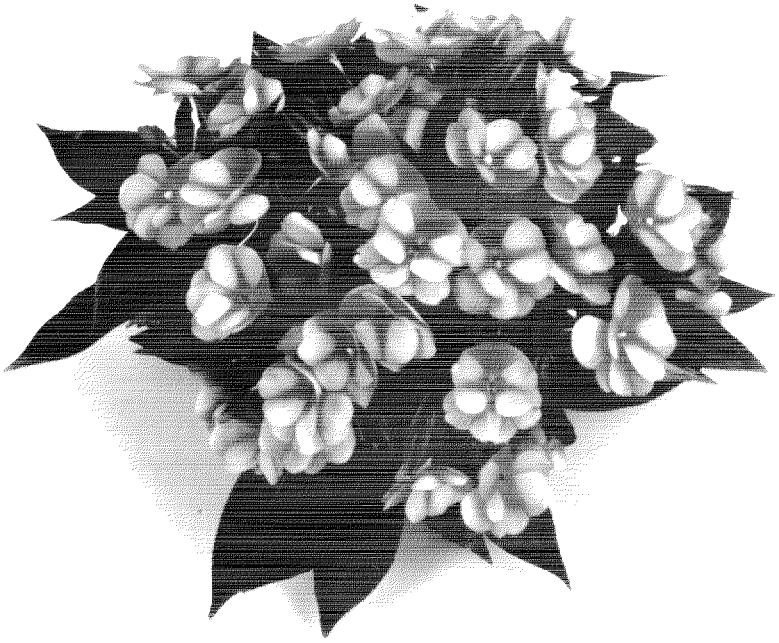

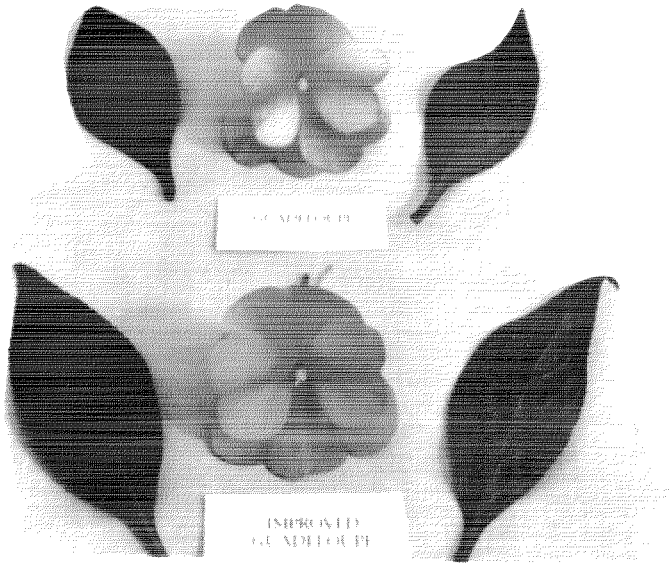
IMPROVED